(12) United States Patent
Dunn et al.

(10) Patent No.: US 10,000,460 B2
(45) Date of Patent: *Jun. 19, 2018

(54) CHELATE-CONTROLLED DIASTEREOSELECTIVE HYDROGENATION WITH HETEROGENEOUS CATALYST

(71) Applicant: THOMAS SWAN & CO. LTD, Durham, Durham (GB)

(72) Inventors: David Dunn, Jarrow (GB); Howard Winston Tyrrell Sutton, Washington (GB); John Ing Chuan Daly, Hexham (GB); Simon Jonathon Grant, Newcastle (GB); Lian Hutchings, Darlington (GB); Patrice Georges Antonin Ribiere, Durham (GB); Matthew Richard Gibbings, Rainton Durham (GB); Sergio Aaron Gamboa Martinez, Newcastle upon Tyne (GB); Craig Anderson, Stanley (GB); Yulia Rogan, Durham (GB)

(73) Assignee: Thomas Swan & Co. Ltd, Durham (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/470,691

(22) Filed: Mar. 27, 2017

(65) Prior Publication Data
US 2017/0197929 A1    Jul. 13, 2017

Related U.S. Application Data

(63) Continuation of application No. 15/302,936, filed as application No. PCT/GB2015/052802 on Sep. 28, 2015, now Pat. No. 9,751,848.

(51) Int. Cl.
C07D 307/02    (2006.01)
B01J 23/58     (2006.01)
C07D 307/12    (2006.01)

(52) U.S. Cl.
CPC ............ *C07D 307/12* (2013.01); *B01J 23/58* (2013.01)

(58) Field of Classification Search
CPC ......... C07D 307/12; B01J 23/58; B01J 20/00; C01B 31/08
USPC ................................. 549/472; 502/411, 427
See application file for complete search history.

(56) References Cited

U.S. PATENT DOCUMENTS

| | | | |
|---|---|---|---|
| 3,784,481 A | 1/1974 | Lassau et al. | |
| 4,115,462 A | 9/1978 | Thelen et al. | |
| 4,577,035 A | 3/1986 | Huffman et al. | |
| 6,015,927 A | 1/2000 | Kiel | |
| 9,751,848 B2 * | 9/2017 | Dunn | C07D 307/12 |
| 2013/0165697 A1 | 6/2013 | Neumann et al. | |

FOREIGN PATENT DOCUMENTS

| | | |
|---|---|---|
| CN | 101502800 A | 8/2009 |
| CN | 103319308 A | 9/2013 |
| EP | 1767520 A1 | 3/2007 |

OTHER PUBLICATIONS

UK Intellectual Property Office Search Report issued in application No. GB1417035.1 dated Mar. 26, 2015.
International Search Report issued in application No. PCT/GB2015/052802 dated Dec. 3, 2015.
Written Opinion issued in application No. PCT/GB2015/052802 dated Dec. 3, 2015.

* cited by examiner

*Primary Examiner* — Taylor V Oh
(74) *Attorney, Agent, or Firm* — Knobbe, Martens, Olson & Bear, LLP

(57) ABSTRACT

A hydrogenation catalyst, preferably palladium on a support, preferably alumina or activated charcoal support, is used in the presence of lithium salts, with salts such as the borates being preferred. This provides hydrogenation of precursors to give rise to a stereoselective, such as diastereoselective bias in the product of alkene hydrogenation using the catalyst.

16 Claims, 1 Drawing Sheet

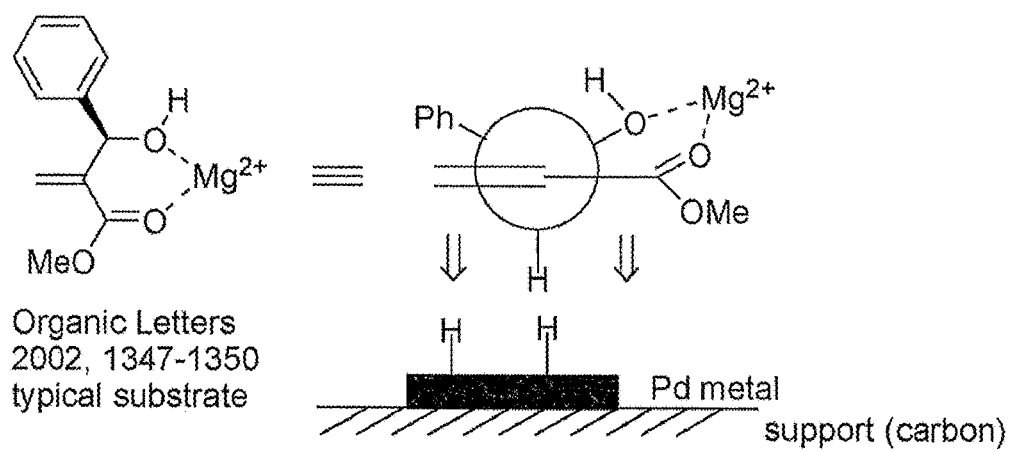

CHELATE-CONTROLLED DIASTEREOSELECTIVE HYDROGENATION WITH HETEROGENEOUS CATALYST

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application is a continuation of U.S. patent application Ser. No. 15/302,936 filed Oct. 7, 2016, which is the U.S. National Phase of International Application No. PCT/GB2015/052802 filed Sep. 28, 2015, designating the U.S. and published as WO 2016/046575 on Mar. 31, 2016 which claims the benefit of GB Patent Application No. 1417035.1, filed on Sep. 26, 2014, the disclosure of each of which is incorporated herein in its entirety by reference.

BACKGROUND

Field of the Invention

The present invention relates to stereoselective hydrogenation and in particular to the diastereoselective hydrogenation of bicyclic alkenes using known and novel hydrogenation catalysts.

Description of the Related Art

Heterogeneous hydrogenation of alkenes is a well-established technique. The mechanism of action of a metal catalyst supported on an inert solid is generally considered to occur through the absorption of hydrogen onto the catalyst metal surface and the subsequent approach of the carbon-carbon double band to that surface giving rise to hydrogen addition across one side of the double band. The planar structure of the alkene is transformed into the well-known tetragonal carbon structure, which may give rise to a particular set of chiral centre(s) depending upon the structure of the parent alkene. Metals used as catalyst are typically nickel, palladium, platinum or other precious metals (platinum group metals). Further review of the art can be found in Erti G., Knoezinger H., Schueth F., Weitkamp J.—Handbook of Heterogeneous Catalysis, John Wiley & Sons Inc., 2008, ISBN: 978-3-527-31241-2. Should the parent alkene be prochiral, hydrogenation in the presence of a heterogeneous metal catalyst is expected to give rise to a racemic mixture of enantiomers. Asymmetric heterogeneous hydrogenation, i.e. providing stereo isomeric products in unequal amounts, using a solid metal catalyst, has not have found the same industrial development as its asymmetric homogeneous hydrogenation counterpart and other strategies such as the use of a chiral modifier (e.g. tartaric acid or cinchonidine derivatives) adsorbed on the metal surface or covalently linked to the solid support of the metal catalyst as described in Murzin D. Y. et all, Catalysis Reviews: Science and Engineering, 2005, 47:2, 175-256, or in Ding K., Uozumi Y.—Handbook of Asymmetric Heterogeneous Catalysis, John Wiley & Sons Inc., 2008, ISBN 978-3-527-31913-8 are preferred as the logical route to influence chiral reaction pathways.

In the case of an unsaturated substrate bearing an existing chirality, the newly formed chiral centre will generate a mixture of diastereoisomers. In the absence of thermodynamic or kinetic controls, or other structural influencing effects, the mixture of diastereoisomers is expected to be a 50/50 mixture.

In some cases a functional group on an unsaturated (i.e. alkene) substrate bearing, or not, existing chirality, will have an asymmetric inductive effect, resulting in the preferential formation of one diastereoisomer aver the another. In Chemical Reviews, 1993, Vol. 93, 1307-1370, Hoveyda et al. describe several examples of directed heterogeneous hydrogenations where a functional group interacts with the metal surface of the catalyst, favouring the approach of the substrate to the catalyst by a specific side, and leading to the delivery of hydrogen to the unsaturation site in a syn fashion (with respect to the directing group). That disclosure provides that "the nature of the directing group, solvent, catalyst, support, and hydrogen pressure" influence the product. In the same paper, hydrogenations with homogeneous catalysts are also discussed, mostly on allylic or homoallylic substrates (cyclic or linear olefins). This method is based on the binding of hydrogen, the alkene unsaturation and the directing group to the metal centre of the catalyst, which is dependent on the electronic structure and configuration of the substrate, the metal and its ligands. Trial and error 'fine tuning' of the directing group (when possible), the catalyst and the reaction conditions is required to provide a good asymmetric induction through experiment. The high design flexibility of homogeneous metal catalysts allows for such fine tuning, but the end result can still prove expensive both in terms of catalyst and process costs (time, temperature, suitability for large scale use) when compared with standard commercial metal catalysts supported on an inert solid.

In Chemical Reviews 1999, 99, 1191-1223, A, Mengel et al. review the use in synthesis of reactions on olefins or carbonyls where the diastereoselectivity is induced by a remote stereocentre, and the different models used to predict their stereochemical outcomes, such as Cram's and Felkin-Anh's rules. Reactions involving an a-chiral double band, i.e. 1,2-induction, are the most common and cover a broad range of chemistry such as nucleophilic additions, electrophilic additions, cycloadditions or radical reactions. Moving the chiral centre to the position of the reaction centre, i.e. 1,3-induction, often requires the use of a chelating agent. In that case, either the reaction centre and the chiral centre are tethered together and the reagent is delivered externally of the chelate or the reagent becomes part of the chelate itself. Most reactions described are limited to nucleophilic additions, including carbonyl reductions with a metal hydride where the carbonyl and the chiral centre with an alcohol or ether functional group are first complexed with a Lewis acid.

BRIEF DESCRIPTION OF THE DRAWING

FIG. 1 shows use of magnesium Bromide as a complexing agent to achieve Pd-catalysed diastereoselective hydrogenation as shown in Organic Letters, 2002, 1347-1350 by A. Bouzide.

In Organic Letters, 2002, 1347-1350 by A. Bouzide (FIG. 1) described the use of magnesium bromide as a complexing agent to achieve the Pd-catalysed diastereoselective hydrogenation of Baylis-Hillman ~-hydroxyester alkenes. The author found the reaction to require stoichiometric amount of a magnesium salt and to be highly dependent on the solvent (no selectivity with MeOH, increasing selectivity for toluene <THF <EtOAc <$CH_2Cl_2$). Furthermore, many of the reaction conditions being quite mild (atmospheric pressure of hydrogen, room temperature for 1 h30) and not suitable for use on a commercial scale due to limitation on reaction control (i.e. inability to remove pressure to stop reaction and high precious metal use) make such methods difficult and expensive industrially (42 wt % Pd/C catalyst loading, 144 wt % or 1.5 mol equivalent MgBr$_2$ loading with regards to substrate).

If the chiral centre responsible for the diastereomeric induction can be pre-existing to the hydrogenation reaction (and its configuration predetermined, as in all three above papers), it could also be formed in situ prior to the final reduction (e.g. when hydrogenating dienes). In the latter case the first (favoured) reduction to take place will provide a racemic mixture of a partially reduced intermediate, but the newly formed chiral centre could influence the formation of the second (final) one, resulting in a diastereoselective reaction.

In specific cases, when generating products with an internal plane of symmetry, such hydrogenation may give rise to a stereoisomers mixture containing a meso isomer. A meso isomer is a non-optically active member of a set of stereoisomers, wherein at least two of the stereoisomers are optically active. In consequence, whilst containing two or more chiral centres the meso isomer is itself not chiral. A meso compound structure is superposable on its mirror image i.e. all aspects of the objects coincide and a meso isomer it does not produce a "(+)" or "(−)" reading in polarimetry.

SUMMARY

Whilst prior art approaches to stereoselective hydrogenation, such as illustrated above, can give high levels of selectivity they generally use complex and expensive methods requiring precursors that themselves require considerable synthesis and are generally only suitable for laboratory (gram) scale synthesis.

There remains a need for a means of influencing hydrogenation using the well-established transition metal catalysts such as nickel, palladium or platinum on readily available supports such as charcoal, which may use simple and readily available adjuncts or auxiliaries to prove stereoselective hydrogenation an industrial scale.

Furthermore desired catalysts should allow the use of a simple experimental methodology (e.g. a one-pot reaction), with a simple work up (e.g. by simple filtration) such as to remove catalyst and auxiliaries from reaction product.

There is a need for new catalysts and alternative methods for the selective hydrogenation of double bonds to provide stereochemical bias in hydrogenated product. Such catalysts are required that are capable of being prepared and used on an industrial scale. Such catalysts having a simple composition or at least a simple and hence economic pathway to preparation are required. Such catalysts with high temperature stability would prove useful. Such catalysts more resistant to poisoning would also prove useful.

The present invention is directed to a means of selective hydrogenation far disturbing the balance away from a statistical mix of diastereoisomers produced in hydrogenation of alkene using a metal catalyst.

There is a further need to provide improved or alternative modified catalysts for general use.

Documents considered relevant to the present invention as identified in the priority application include US 2013/0165697 which discloses a method for hydrogenating phenols to cyclic ketones by hydrogenation using a palladium on carbon catalyst treated with one of sodium carbonate, lithium carbonate, sodium acetate or lithium acetate.

More specifically, US 2013/0165697 application describes the use of alkali doped Pd/C catalyst(s) to selectively reduce phenol compounds to the corresponding ketones products, in good yield when using their solution in an alcohol solvent. All 17 examples described the use of a broad range of weakly basic alkali salts (either lithium, sodium, potassium as cation, and carbonate or acetate as anion). All these various salts can influence the reaction pathway, i.e. limit the formation of side-products and over-reduction to the cyclohexanol derivatives to provide a good yield of the ketone products. But none these alkali doping agents demonstrate any stereocontrol on the considered reaction nor is any particular pattern in their effectivity evident.

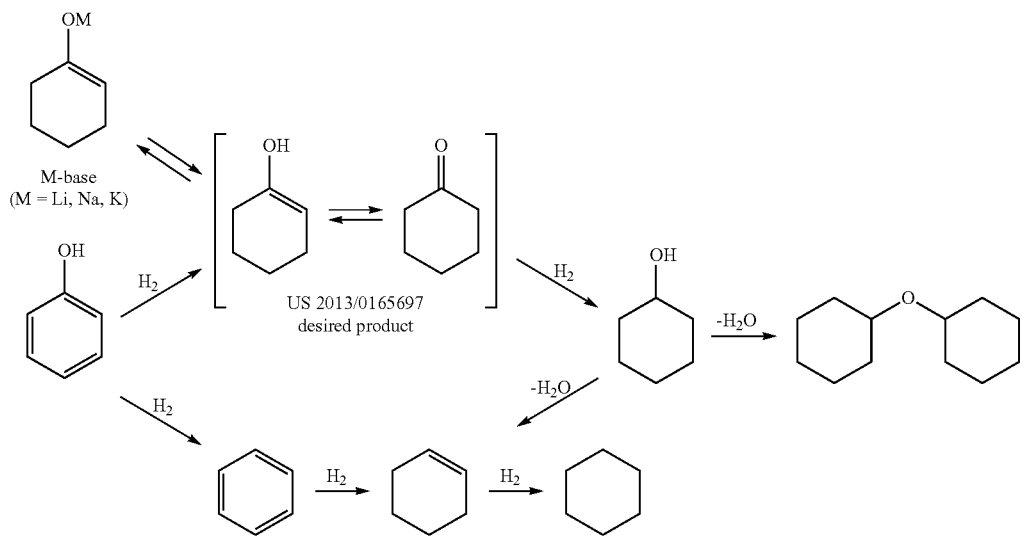

Scheme derived from G Neri and all, Applied Catalysis A: General 11 (1994) 49-59 CN 101502800 discloses the use of a palladium on carbon with an alkaline metal or alkaline earth metal auxiliary catalytic component for synthesising alkyl cylohexanone from alkyl phenols. U.S. Pat. No. 6,015,927 discloses the use of a palladium on carbon catalyst with a borax auxiliary component for preparing cyclohexanone from phenols.

In view of the above there is a further need to provide improved or alternative modified catalysts for general use and in particular to influence the stereochemical pathway of hydrogenation.

Products of the hydrogenation process described herein find commercial application such as disclosed in U.S. Pat. No. 5,550,200 in relation to rubber manufacture. As such, relatively small percentage changes in diastereoselectivity can be commercially useful as a product with application on a large industrial scale.

The present invention in its various aspects is as set out in the appended claims.

In the various aspects of the present invention diastereoselective hydrogenation of a specific substrate is provided. The hydrogenation is mediated by a catalyst supported on a substrate and in conjunction with an auxiliary catalytic component also termed herein the Salt. The meaning of those terms will now be provided before using these meanings to specify the present invention:

Substrate

In the present invention provides the diastereoselective hydrogenation of bicyclic dienes of the form shown in formula (1).

(1)

Wherein Cycl represents a cyclic moiety and $R^1$ represents H or a further organic chemical moiety and wherein hydrogenation of the alkene provides a meso isomer.

In formula 1, Cycl represents an unsaturated moiety being a five or six membered heterocyclic ring, wherein the heteroatom is one of O, S, N or P. The heteroatom is preferably O. Cycl is preferably selected from furan ($C_4H_3O$—), 4H-pyran ($C_5H_6O$—) ring moiety. Cycl is still more preferably furan and yet more preferably linked at the 2 position (i.e. adjacent the oxygen). The most preferred substrate is 2,2'-di(2-tetrahydrofuryl)propane, also known as 2,2-difurylpropane. Hitherto, provision of specific stereoisomers of this material has been achieved by obtaining product from routine hydrogenation using a platinum group metal catalyst on charcoal and subsequent separation by chromatography. Such a route is not viable far industrial scale, multi-ton production. The present invention addresses this need.

In formula 1, $R^1$ preferably represents an organic chemical moiety of molecular weight less than 500 Da, preferably less than 128 Da, this limit reduces and in the latter case avoids unduly bulky groups which may inhibit interaction with the catalyst surface.

Independently of molecular weight, $R^1$ represents H or an achiral organic chemical group, preferably an alkyl chain. The alkyl chain may be optionally substituted with O, S, N or P based functionality but this is not preferred as it may influence catalysts selectivity. More preferably $R^1$ represents H or a $C_1$ to $C_6$ alkyl chain, optionally but not preferably, substituted with O, S, N or P based functionality. When $R^1$ represents H or a $C_1$ to $C_6$ alkyl chain it is speculated that the primary interaction with the catalytic composition of the invention (i.e. the combination of catalyst, substrate and Salt) is optimised to give the highest stereo selectivity. The most preferred $R^1$ is H or $CH_3$, this is thought to arise due to its low stereochemical bulk enabling optimum interaction between the catalytic composition.

Whilst formula 1 may comprise any combination of the moieties mentioned in the previous paragraphs a preferred combination is wherein Cycl provides alpha, beta unsaturation to the double band and $R^1$ represents a C1 to C6 alkyl chain.

1,3-induction via a chelate with lithium salts at a catalyst/substrate surface is thought to be involved. The compound may be thought of as a compound that provides two prochiral Csp2 centres on separate unsaturations and not part of the same ring.

The Catalyst

The catalyst component of the catalyst composition in the present invention is a metal, and specifically a metal hydrogenation catalyst, which is preferably selected from platinum, palladium, rhodium, ruthenium and nickel, more preferably selected from platinum, palladium, rhodium and ruthenium in providing higher selectivity. The metal catalyst is preferably palladium. Palladium provides the highest stereochemical selectivity in the catalyst composition in the present invention.

It will be appreciated that the metal catalyst whilst normally an preferably provided as the pure metal may be provided as in other oxidation state known to be effective far hydrogenation catalysis. In particular, a precursor, such as a metal oxide for subsequent reduction such as to provide in situ metal may be used, an example being palladium oxide.

The catalyst component preferably comprises no more than a trace, less than 100 ppm, preferably less than 10 ppm, of non-catalyst metal. The catalyst preferably comprises no more than a trace, less than 100 pmm, preferably less than 10 ppm, of other anions ions besides chloride bromide or carbonate. Ppm herein is ppm by weight (mg/kg).

The Support

The catalyst, a hydrogenation catalyst, of the present invention is supported upon a Support in conjunction with the Salt to provide the catalyst composition in the invention. The support is a solid.

The support may be any inert support catalyst carrier known to be suitable as a support for the catalyst of the present invention. Preferred supports are carbon, alumina, silica, titanium dioxide, calcium carbonate, lithium aluminate and barium sulphate. More preferred supports are carbon (such as in the form of charcoal), silica and alumina. If the preferred support is carbon, more preferred is amorphous carbon and most preferred the support is charcoal. The most stereoselective support is Alumina. Results have shown that the specific form of palladium on charcoal, as reflected in comparison of supports from different suppliers has a minimal effect on stereoselectivity of hydrogenation. This effect is in the order of 6% by weight in stereoisomer product, this against a repeatability of around 2% by weight stereoisomer product between repeat experiments under nominally identical conditions.

The support preferably has a surface area of from 10 to 1500 m2/g, preferably from 500 to 1500 m2/g, most preferably from 1000 to 1500 m2/g.

The Support is preferably provided in a particulate form with a particle size below 1 mm, the support is more preferably of particle size between 1 and 100 μm, as measured using light scattering using a Malvern mastersizer (™) by the 04.3 measure.

Catalysts of the type suitable for use in the present invention in conjunction with the support may be provided with an inert coating to facilitate storage. Whilst this material is preferentially removed prior to use such material has in practice shown negligible effect on catalyst performance. The catalyst on the substrate is preferably provided in a liquid reaction mixture, most preferably as a slurry, this appears to provide a maximum reaction rate. However, an immobilised support washed aver by reaction medium in liquid or gaseous form is also a possibility.

The catalyst in conjunction with the support used in the present invention is for the catalysis of hydrogenation using hydrogen gas. Such hydrogenation is well known to the skilled person in the art in the hydrogen gas is provided under pressure in a sealed container, preferably with agitation, in a conventional manner. The hydrogen used is 99.9% pure or better.

The Salt (Auxiliary Catalytic Component)

While salts are known in conjunction with supported hydrogenation catalysts to influence reaction products for hydrogenating a substrate the use of such salts to alter the stereochemistry of the reaction products is not known. The mechanism by which such salts influence reaction mechanism is a matter of speculation and experimental investigation has provided several surprising and unpredicted influences of salt type.

The Salt of the present invention may also act as the support for the catalyst. However, results indicate that each of the catalyst, the support and the Salt may contribute to selectivity and therefore a combination of the three features as separate materials is preferred, i.e., wherein each of the catalyst, support and Salt are chemically different materials (whether or not they are physically aggregated).

The salt is a lithium salt. The lithium salt may be an organo-carboxylate, an organo-sulphate, and aluminate, chloride, bromide, carbonate, hydroxide or barate. The salts may be hydrated salts. The lithium salt is preferably a metaborate, tetraborate, chloride, bromide, hydroxide, organo-carboxylate (preferably RC02) Preferable carboxylates are the acetate, benzoate, oxalate and palmitate, more preferable carboxylates are the acetate, benzoate and palmitate. A mixture lithium anions may be used.

The preferred salts are the metaborate, tetraborate, chloride, hydroxide and benzoate. The preferred salt may be metaborate, tetraborate, giving a high degree of conversion and selectivity.

The most preferred lithium salts are the tetraborate, anhydrous metaborate, metaborate monohydrate or dihydrate. The hydroxide has been found in some instances to give rise to undesirable byproducts, thought to be due to its highly alkaline nature.

The lithium salt, and the reaction composition as a whole, preferably does not comprise any divalent or trivalent metal ions as these appear to reduce selectivity. The catalyst composition and the reaction composition as a whole preferably consists of lithium salt as the only inorganic cation. More preferably the catalyst composition consists of lithium salt as the only inorganic cation.

Catalyst Composition

The catalyst composition of the invention comprises the catalyst, the support and the salt.

The loading of the catalyst on the support is preferably from 0.25% to 25% by weight, more preferably in the range 1% to 10%, most preferably 2 to 5%. As noted, the support itself can influence upon the stereoselectivity of hydrogenation can the catalyst and the salt. As such high loadings of catalyst on the support (>10%) appear to mask the support with which the salt adjunct is thought to possibly interact and seem to reduce the selectivity effect. The most preferred catalyst loading is therefore in the range 2 to 5% as there is a balance between catalyst, substrate and Salt contributions to selectivity.

The combination of catalyst on support is a solid and as mentioned may be in the form of a powder. However, the powder may be aggregated in the form of a pellets (for example an aggregate of particles forming the unit of dimensions from 1 to 10 mm) or as a pastes, such as a water based paste.

The catalyst composition preferably comprises Salt at the level of 1 to 600 mole equivalent with respect to the catalyst, preferably at 5 to 300 mole equivalent with regards to the catalyst, most preferably at 5 to 100 molar equivalents with respect to the catalyst. It been recalled that for the purposes of the definition in the present invention the catalyst is the metal presented on the support rather than the combination of catalyst with support and/or Salt.

Catalyst Composition Preparation

The present invention requires a combination of the catalyst, the support and the Salt as mentioned above. This combination of materials may be prepared as follows:

Loading of catalyst on to support substrate is by known techniques. Loading a catalyst onto the support is preferable prior to any subsequent step in catalyst composition preparation.

Combining the catalyst on the support with the Salt may take place during catalyst preparation (for example by co-precipitation or co-impregnation support with catalyst), prior to reaction (for example by pre-mixing or pre-contacting the catalyst on the support with salt as a physical mixture) or immediately prior to reaction (catalyst and salt charged separately at the start of the reaction), i.e. prior to the introduction of hydrogen. Combination of the catalyst on the support with the Salt is most preferably prior to reaction or during reaction or most preferably during reaction (catalyst and salt charged separately at the start of the reaction), this appears to give the most facile reaction condition set up and good selectivity.

An alternative is where the support and the Salt are the same material as mentioned previously. A methodology to achieve this may be adapted from the art such as disclosed in EP074421381 which describes the preparation of a palladium catalyst supported on solid lithium aluminate.

Reaction Conditions

The various aspects of the present invention may be performed under the following reaction conditions:

In the absence of any solvent when the substrate is present as a gas or liquid at the temperature of reaction. This has the advantage of not requiring solvent removal on subsequent workup of the reaction mixture. Preferably a liquid solvent is used, preferred solvents are: alkanes and in particular $C_4$ to $C_8$ alkanes; aromatic solvents in particular toluene, halogenated solvents in particular dichloromethane; palar non-protic solvents such as ethers in particular methyl tert-butyl ether (MTBE) or tetrahydrofuran (THF); esters, in particular ethyl acetate, and palar protic solvents in particular alcohols (more preferably methanol, isopropanol); or water. The preferred solvents are heptane, MTBE, THF, ethyl acetate, methanol, ethanol, n-propanol and isopropanol. Most preferred is isopropanol as this provides the higher selectivity.

When a solvent is used it is preferably used in a quantity equivalent to 5 times or less the volume of the substrate, preferably equivalent to 0 to 2 times the volume of the substrate, most preferably from 0 to 1 times the volume of the substrate. A solvent is preferably used when the substrate is not liquid at the reaction temperature. When the substrate is not liquid at the reaction temperature the solvent is used of a type and a quantity so as to dissolve the substrate at the reaction temperature. A liquid which does not dissolve the substrate is not a solvent for the purposes of the present invention. Water may be used but this is not a solvent for many substrates but may, nevertheless, be used (or be present) as an effective biphasic system can result.

The temperature range of the present invention for performing the method and use of the catalyst in the hydrogenation reaction is 10 to 200° C., and preferably between 50° C. and 120° C.

The pressure used for performing the method and use of the catalyst in the hydrogenation reaction of the present invention is above 100 kPa, preferably above 200 kPa, most preferably above 500 kPa. The pressure of reaction may be in the range 100 kPa to 70 MPa (1 to 700 bar), preferably 200 kPa to 5 MPa (2 to 50 bar), more preferably 500 kPa to 1200 kPa (5 to 12 bar). Higher pressure provides greater selectivity.

The reaction time of the present invention used for performing the method and use of the catalyst in the hydrogenation reaction is 6 to 48 hours, preferably 6 to 24 hours, most preferably 18 to 24 hours. The reaction time is not understood to influence selectivity but has a greater influence on total reaction conversion of substrate.

Reactions of the present invention generally go to completion or near completion and the time ranges indicated when using representative temperatures and pressures particularly with respect to the catalyst used, as known in the art.

The skilled person will readily establish by trial and error a reaction time suitable to give a required conversion of materials based upon the parameters provided above.

Whilst the experimental data provided use a batch reaction it is considered that a continuous reaction, such as aver a bed of immobilised catalyst composition could be equally applicable.

The present invention has been developed with stirred reactors, but it is understood by the man of the art that such a diastereoselective heterogeneous reaction could be adapted to other plant hydrogenation equipment such as Buss®-loop or jet-loop reactors or flow reactors such as multi-plate reactors (e.g. as some manufactured by Alpha-Laval) as these reactors are known to be able to handle the catalyst slurry and to provide extra temperature and mixing (with impact on mass transfer and reaction rate) controls.

DETAILED DESCRIPTION

The present invention will now be further defined in the light of the terms, the meaning of which has been described, such as above.

The first aspect the present invention is a method of stereoselective hydrogenation, the method comprising providing the substrate, the catalyst, the support and the salt as defined above and carrying out a hydrogenation of the substrate using hydrogen.

The preferred reaction conditions being also as mentioned above.

The method of the first aspect of the present invention may provide the steps:

a) providing the catalyst on the support;

b) contacting the catalyst with the Salt; to provide a modified catalyst;

c) providing the substrate according to equations (1) far hydrogenation, the substrate being capable of hydrogenation to give rise to give stereoisomers;

d) contacting the modified catalyst and the alkene with hydrogen;

e) hydrogenating the alkene using the aforementioned reaction conditions.

This aspect of the invention is further details in the claims.

In a second aspect of the present invention there is provided the use of the catalyst, the support and the salt as defined above for the stereoselective hydrogenation of the substrate as also defined above. The use may provide greater than statistical meso isomer hydrogenation product, more preferably greater than 52%, and still more preferably greater than 57% and greater than 70%. This use has been shown to be particularly effective in providing higher diastereoisomer (and particularly mesa) hydrogenation product in comparison to statistical i.e. (50/50) and higher than reference (i.e. untreated catalyst) in stereoselective hydrogenation.

This aspect of the invention is further details in the claims.

The third aspect the present invention is a catalyst on a support in combination with the Salt, all as defined above with the limitation that the salt is one or more of lithium metaborate or tetraborate.

These novel catalysts have been shown to be particularly effective in diastereoselective hydrogenation compared to known catalyst modification materials such as described in the prior art cited above and also provide high levels of conversion.

This aspect of the invention is further details in the claims.

The present invention is exemplified by the following reaction using the most preferred substrate:

Equation 1

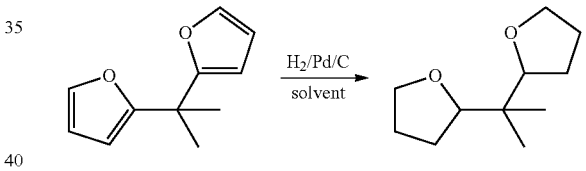

This general reaction is disclosed in U.S. Pat. No. 4,577,035 and in George W. Huffman, et al., "2,2'-isopropylidine bis(tetrahydrofuran)", U.S. Pat. No. 4,577,035 (1986). The reaction gives rise to the following stereoisomeric products:

Equation 2

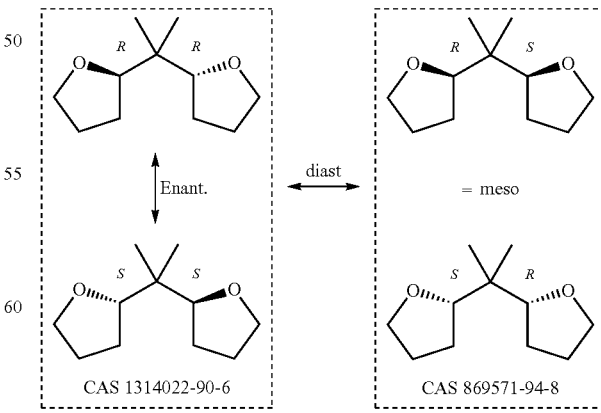

This reaction conditions disclosed in U.S. Pat. No. 4,577,035 and when repeated gives rise to a statistical composition of stereoisomers. Specifically, the ratio of 1:1:2 of the R,R, the S,S and the meso isomers.

The above material, 2,2'-di(2-tetrahydrofuryl)propane, also known as 2,2-difurylpropane, 2,2'-isopropylidene bis (terahydrofuran), OOPS and DTHFP has several uses including as a palar modifier in butadiene polymerisation. Such uses are disclosed in many documents, including U.S. Pat. No. 5,698,646, WO2009/134665 and EP 1462459 and WO2012119917 A. The material is used industrially on a large scale and can be produced by means of the above hydrogenation reaction.

WO2011/087841 discloses improved utility for the meso isomer of 2,2-di(2-tetrahydrofuryl)propane. However, despite the potential for such a material no selective synthetic route for production of the meso isomer is available.

bicyclic ether dienes, using 2,2-di(2-furyl)propane as a substrate target, this need is met by the present invention.

There is also a need for the stereoselective hydrogenation of alpha-beta unsaturated ethers this need is met by the present invention Whilst it was thought that the effect was due to the presence of a group one metal ion this does not appear to be the case as the effect is not found with other group one ions, such as sodium and potassium and certainly not by di or trivalent metal ions.

Whilst not wishing to be bound by theory the present invention is thought to utilise the following reaction pathways:

Equation 3

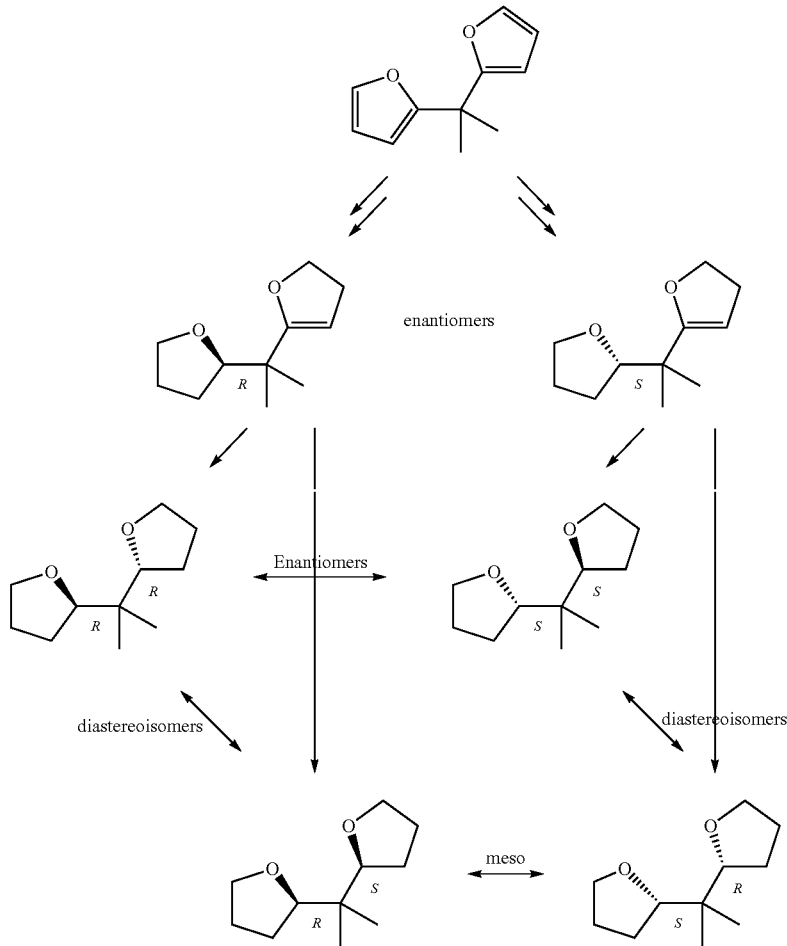

Production being based upon separation of the statistical stereoisomeric mixture by physical means. This is wasteful of the undesired R,R and S,S isomers.

It has been surprisingly found that the use of lithium salt modified palladium and platinum on charcoal can be used to hydrogenate 2,2-di(2-furyl)propane to give 2,2'-di(2-tetrahydrofuryl)propane as the meso isomer at more than 70% by weight.

Therefore there is a specific need for a means for the diastereoselective hydrogenation of 1,4 bicyclic dienes, starting from the selective hydrogenation of unsaturated heterocycles with the specific starting point being a 1,4

As such the selectivity of hydrogenation is expressed at the level of hydrogenation of di(2-furyl)propane.

Experimental

Analytical Methods:

In the following the analytical methods the identity of the products was established using H1-NMR spectroscopy using a Varian 500 MHz as described in patent U.S. Pat. No. 9,062,017B2, and GC-MS analysis carried out with a Shimadzu GC-2010 equipment using known standards and known samples of product as reference. Mass spectrometry (MS) detection was performed using a Shimadzu GCMS-QP201 O plus in electron ionisation mode (interface temperature at 250° C. and the ion source at 240° C.). GC-MS was run using a RTX-624Sil MS column, helium (linear velocity of 40 cm/s) as carrier gas, an injection at 290° C. (with a split ratio of 10) and the following temperature ramp: 60° C. far 5 min, ramping up at 10° C./min to 320° C.

Hydrogenation output routine analysis was carried out by GC-FID using an Agilent 6890 equipment with flame ionisation detection (FIO). GC-FID was ran using a RTX-624Sil MS column, hydrogen (constant pressure 5.8 psi) as a carrier gas far GC-FID, an injection at 290° C. (with a split ratio of 10) and the following temperature ramp: 60° C. far 5 min, ramping up at 10° C./min to 320° C., and held for 5 min. The detector temperature was set at 280° C. DTHFP GC profile shows two separated peaks with different close retention times corresponding to the two diastereoisomers. Meso diastereoisomer correspond to the peak with the lowest retention time, the sample being validated by the analysis methods in the previous paragraph.

Meso diastereoisomer ratio in the following is expressed as:

$$meso\ \% = \frac{meso\ DTHFP\ isomer\ (R,S,\ or\ S,R)GC\ area\ \%}{all\ DTHFP\ isomers\ (R,S\ or\ S,R/S,S/R,R)GC\ area\ \%}.$$

The experimental work showing in tables 1 and 2 was performed using a Biotage Endeavor®, an automated catalyst screening system with reactors setup in parallel.

Each reactor has a working volume up to 7 ml, is equipped with an internal glass tube and a paddle stirrer, and can withstand pressures of up to 50 bars.

2,2-di(2-furyl)propane (DFP) (1.575 g, 8.94 mmol) with 31.5 mg of wet catalyst (commercial 5% Pd/C, 50% water), at 2 wt %, to which was added commercial powdered inorganic salts (0.5 mole equivalent of the cation vs DFP). With respect to the results in table 1 and 2, the contents were heated with with stirring set at 850 rpm, under hydrogen (5 bar) for 18 hours at 60° C. Using the above method the following results and the following molecules: Catalysts, salts, substrate were added to the glass tubes and transferred to the reactor. The carousel was sealed and tested for leaks with nitrogen, then purged three times with hydrogen. The reaction was deemed to start once the target temperature was reached and stabilised. After the 18 hours, the heating was stopped. Once back at room temperature, the pressure was released, the carousel opened and an aliquot of the reaction crude was filtered and analysed as below. Variations in the method are carried out at equal molarity of reactants.

The results are shown below, variation in the method being as needed to accommodate the definitions in the table.

TABLE 1 metal catalyst substrate variability and underlying effect

| Starting material | Product % Meso isomer |
|---|---|
| no Lithium Chloride 12 catalysts within the definition provided in the experimental screened to show catalyst to catalyst variability. Catalysts obtained from Johnson-Matthey, BASF, Hindoustan Platinum and Evonik. | 40-48% depending on Pd/C type and commercial sources |

TABLE 1-continued metal catalyst substrate variability and underlying effect

| Starting material | Product % Meso isomer |
|---|---|
| no Lithium Chloride using two specific Pd/C catalysts (two different suppliers) retained for the rest of the experimental data presented herein. | 42-45% |
| Lithium Chloride | 68% |

The effect of the alkali metal salt on the hydrogenation of DFP is as detailed in table 2 and provides:

TABLE 2 salt additive screening

| Metal salt | Product % Meso isomer |
|---|---|
| No metal salt additive | 42-43% |
| Lithium Chloride | 64-68% |
| Lithium Bromide | 51% |
| Lithium Carbonate | 59% |
| Lithium Acetate | 57% |
| Lithium (tetra) Borate | 60% |
| Lithium Metaborete | 64% |
| Sodium Chloride | 43% |
| Potassium Chloride | 42% |
| Aluminium Sulphate | 43% |
| Manganese (II) Chtoride | 45% |
| Copper (I) Chloride | 46% |
| Copper Sulfate | 43% |
| Zinc (II) Acetate | 43% |
| Ammonium Chloride | 43% |

Only salts with a lithium cations show a significant increase of the meso diastereoisomer in the reaction product. The Salt of the present invention is a lithium salt.

The product further comprised a 50/50 mixture of the R/R and S/S isomers, this was established in preliminary experiment and has been assumed in the results shown in table 3 onward. The yield in each case was 60% hydrogenation products or above.

Low reaction yield (in the order of 60%) on equivalent conditions as relevant to table 3 was evident with lithium chloride and lithium hydroxide, as compared to salts such as the meta and tetraborate at clearly above 60%.

Further experimental data in the following tables was acquired using a stainless steel 10-pot parallel reactor ("carousel"). This equipment can withstand pressures of up to 50 bars, heating and stirring are provided with a standard hotplate stirrer, with each 30 ml-reaction cell having its own magnetic cross-shaped fly and a glass tube fitting the inside of the cell. Typical reaction volume was 6 ml to allow enough head space for the reacting gas.

Stirring was set at 1200 rpm. Reactions were performed in reaction tubes containing 6 g of material, using DFP [2,2-di(2-furyl)propane] as substrate, a catalyst loading of 0.5 to 2%, powdered lithium salts (5 to 600 mole equivalent vs the metal of the catalyst), solvent at O to 2 volumes against substrate, temperatures from 60 to 100° C., and hydrogen pressures from 1000 to 3000 kPa (10 to 30 bar). The method was otherwise as disclosed in more detail far table 1. As such the variation in % meso isomer product reflects those differences in condition. The catalysts were used at 2 to 5% w/w metal on the named substrate with the exception of Nickel at 22% w/w on silica.

Table 3—Variation of Metal Catalysts and Supports

Particular experimental details: Reactions carried out with no salt or with an amount of salt of 2 to 100 equivalents of Li against catalyst metal. Pressures from 10 to 30 bar.

TABLE 4 screening focussed on Lithium salt and variation from the counteranion

| Metal | Support | Li salt | % Meso isomer in product |
|---|---|---|---|
| Palladium | Charcoal | none | 40-46% |
| Platinum | Charcoal | none | 42-50% |
| Palladium | Alumina | none | 44-46% |
| Ruthenium | Charcoal | none | 44-51% |
| Nickel | Silica | none | 48-50% |
| Rhodium | Charcoal | none | 49-51% |
| Ruthenium | Charcoal | $LiBO_2$ | 50-61% |
| Platinum | Charcoal | $LiBO_2$ | 51-67% |
| Rhodium | Charcoal | $LiBO_2$ | 52-67% |
| Nickel | Silica | LiCl | 55-62% |
| Palladium | Charcoal | $LiBO_2$ | 58-82% |
| Palladium | Alumina | LiCl | 60-70% |

We may say that conversion will also be function of the hydrogen pressure with Ru, Rh, Pt, requiring high pressure for high conversion as compared to Pd.

Particular experimental details: The catalyst used was 5% Pd/C 50% wet with a loading of 1 to 2% w/w in regards to the starting material. The salts used at equivalent molar amounts of 5 to 100 equivalents of Li to Pd.

TABLE 5 variation of solvents

| Salt | Product % Meso isomer |
|---|---|
| None | 40-46% |
| $Li_2C_2O_4$ | 51-52% |
| $Li_2CO_3$ | 51-57% |
| LiCl | 56-74% |
| LiOBz | 58-68% |
| $LiC_{18}H_{31}O_2$ | 58-74% |
| $Li_2B_4O_7$ | 58-78% |
| $LiBO_2$ | 58-82% |
| $LiBO_2 \cdot H_2O$ | 75-80% |
| LiBr | 77-78% |
| LiOH | 79-84% |

$Li_2C_2O_4$—lithium oxalate,
LiOBz—lithium benzoate,
$LiC_{16}H_{31}O_2$—lithium palmitate Method as per Further experimental data method. Particular experimental details: The catalyst used was 5% Pd/C 50% wet with a loading of 1 to 2% w/w in regards to the starting material. The salts used at equivalent molar amounts of 5 to 100 equivalents of Li to Pd metal. Pressures from 10 to 30 bar.

TABLE 6 variation in reaction temperature

| Salt | Solvent | Product % Meso isomer |
|---|---|---|
| LiBO2 | DCM | 58-60% |
| LiBO2 | EtOAc | 62-64% |
| LiBO2 | THF | 62-81% |
| LiBO2 | IPA | 66-82% |
| LiBO2 | Heptane | 74-76% |
| LiBO2 | MTBE | 74-76% |
| LiCl | IPA | 56-73% |
| LiCl | Heptane | 64-70% |
| LiCl | MTBE | 68-69% |
| LiCl | THF | 70-72% |
| LiOBz | MTBE | 59-61% |
| LiOBz | IPA | 59-65% |
| LiOBz | Heptane | 60-62% |
| LiOBz | THF | 64-68% |

Method as per Further experimental data method with temperature as shown in table. Particular experimental details: The catalyst used was 5% Pd/C 50% wet with a loading of 1 to 2% w/w in regards to the starting material. The salts used at equivalent molar amounts of 5 to 130 equivalents of Li to Pd metal. Pressures from 10 to 30 bar.

TABLE 7 variation in reaction pressure

| Salt | Temperature | Product % Meso isomer |
|---|---|---|
| $LiBO_2$ | 60 | 66-68% |
| $LiBO_2$ | 80 | 58-78% |
| $LiBO_2$ | 100 | 74-82% |
| $LiBO_2$/LiOBz | 60 | 57-65% |
| $LiBO_2$/LiOBz | 80 | 62-64% |
| $LiBO_2$/LiOBz | 100 | 64-79% |
| $LiBO_2$/LiCl | 80 | 76-78% |
| $LiBO_2$/LiCl | 100 | 73-80% |

Method as per further experimental data method with pressure as shown in table. Particular experimental details: The catalyst used was 5% Pd/C 50% wet with a loading of 1 to 2% w/w in regards to the starting material. The salts used at equivalent molar amounts of 5 to 130 equivalents of Li to Pd metal.

TABLE 8 binary mixture of salt effect - synergetic effect

| Salt | Pressure kPa/100 (bar) | Product % Meso isomer |
|---|---|---|
| $LiBO_2$ | 10 | 66-82% |
| $LiBO_2$ | 15 | 58-78% |
| $LiBO_2$ | 30 | 74-77% |
| $LiBO_2$/LiOBz | 10 | 57-79% |
| $LiBO_2$/LiOBz | 15 | 62-65% |
| $LiBO_2$/LiOBz | 30 | 73-75% |
| $LiBO_2$/LiCl | 10 | 73-80% |
| $LiBO_2$/LiCl | 15 | 76-78% |
| $LiBO_2$/LiCl | 30 | 79-80% |

Higher reaction pressure increases selectivity far meso production.

Particular experimental details: The catalyst used was 5% Pd/C 50% wet with a loading of 1 to 2% w/w in regards to the starting material. The salts used at equivalent molar amounts of 5 to 130 equivalents of Li to Pd metal.

TABLE 9 variation in the equivalent of Li with regards to Palladium metal

| Salt 1 | Salt 2 | Solvent | Product % Meso isomer |
|---|---|---|---|
| LiBO$_2$ | LiOBz | THF | 57-72% |
| LiBO$_2$ | LiOBz | Heptane | 60-74% |
| LiBO$_2$ | LiOBz | IPA | 62-79% |
| LiBO$_2$ | LiOBz | MTBE | 69-75% |
| LiBO$_2$ | LiOBz | None | 71-74% |
| LiBO$_2$ | LiCl | MTBE | 73-74% |
| LiBO$_2$ | Li2B4O7 | IPA | 73-80% |
| LiBO$_2$ | LiCl | Heptane | 74-75% |
| LiBO$_2$ | Li2CO3 | IPA | 75-80% |
| LiBO$_2$ | LiCl | THF | 76-77% |
| LiBO$_2$ | LiCl | IPA | 76-80% |
| LiCl | LiOBz | THF | 67-68% |
| LiCl | LiOBz | Heptane | 68-69% |
| LiCl | LiOBz | MTBE | 68-69% |
| LiCl | LiOBz | IPA | 71-72% |

Particular experimental details: The catalyst used was 5% Pd/C 50% wet with a loading of 1 to 2% w/w in regards to the starting material. The salts used at equivalent molar amounts of 5 to 130 equivalents of Li to Pd metal. IPA is used as solvent at O or 1 volumes against substrate. The salt is lithium chloride.

TABLE 10

Alternative methods of addition of the lithium salt.

| Li Mole equivalents with respect to Pd metal | Product % Meso isomer |
|---|---|
| none | 40-46% |
| 0.5 | 47-48% |
| 1.0 | 51-53% |
| 2.0 | 52-53% |
| 5.0 | 56-71% |
| 10 | 64-65% |
| 50 | 66-73% |
| 300 | 74-75% |

In normal conditions, addition of the salt to the reaction vessel occurred either before or after the addition of catalyst in to the dry vessel (Control reaction). Substrate and solvents were added afterwards. Other methods of addition were tested such as stirring the reaction mixture for 6 days under room temperature and atmosphere before pressurising the vessel (Stirring reaction mixture); grinding the catalyst and the salt into a mixture of powders (Ground mixture of powders); and creating a suspension of the catalyst and salt using an appropriate solvent which was later dried under vacuum (Dried suspension).

Particular experimental details: The catalyst used was 5% Pd/C 50% wet with a loading of 2% w/w in regards to the starting material. The solvent is IPA at 1 volume against the starting material, unless stated otherwise. The first two entries correspond to reactions carried out in a 1-L Parr reactor at 100 C and with 10 bar of hydrogen pressure. Other entries correspond to reactions performed in the Baskerville® carousel described earlier. Temperature for the latter reactions was in the range of 60 to 100 C, and pressure from 6 to 15 bar.

| Solvent | Salt | Eq. of Li vs. Pd | Method | % Meso isomer of the product |
|---|---|---|---|---|
| IPA | LiOBz | 5 | Stirring reaction mixture | 56-57% |
| IPA | LiOBz | 5 | Control reaction | 60-61% |
| IPA | LiBO$_2$ | 50 | Ground mixture of powders | 77-78% |
| IPA | LiBO$_2$ | 50 | Control reaction | 66-82% |
| IPA (trace) | LiCl | 0.2 | Dried suspension | 42-43% |
| IPA (trace) | LiCl | 1 | Dried suspension | 51-52% |
| IPA (trace) | LiCl | 5 | Dried suspension | 60-61% |
| IPA | LiCl | 5 | Control reaction | 49-61% |
| IPA (trace) | LiCl | 50 | Dried suspension | 69-70% |
| IPA | LiCl | 50 | Control reaction | 66-73% |
| Water/IPA (trace) | LiOH | 5 | Dried suspension | 66-67% |
| Water/IPA (trace) | LiOH | 100 | Dried suspension | 74-75% |
| IPA | LiOH | 100 | Control reaction | 83-84% |

In most cases, the use of a different method to mix the catalyst with the salt yielded similar results to the simple addition of the components to the reaction vessel, or at the least, are inside the experimental error.

The article published by Bouzide states that the use of magnesium bromide as additive in the hydrogenation of Baylis-Hillman adducts using Pd/C and a suitable solvent (DCM being the most effective), allows for an increment of stereoselectivity of the hydrogenated product. Experiments to test this salt and the solvent were carried out in the Baskerville reaction both using the conditions stated in the published article and our preferred conditions as specified above in the experimental conditions of table 1.

Particular experimental details: The catalyst used was 5% Pd/C 50% wet. The solvent was DCM at 50 volumes for the first two entries of the table and at 1 volume for the last two, against the starting material. The first entry corresponds to the results published by Bouzide; those reactions were performed at room temperature and atmosphere of hydrogen. The remaining entries show the results acquired from using the Baskerville carousel described earlier. Temperature for the latter reactions was 80° C. and hydrogen pressure 15 bar.

| Substrate | Catalyst w/w % | Salt | Eq. of Li vs. Pd | % Meso isomer of the product |
|---|---|---|---|---|
| Baylis-Hillman | 46 | MgBr$_2$ | 80 | 96-99% |
| DFP | 46 | MgBr$_2$ | 80 | 44-45% |
| DFP | 2 | MgBr$_2$ | 50 | 43-44% |
| DFP | 2 | LiBO$_2$ | 50 | 58-59% |

Results from our experiments point to MgBr2 not being as effective as Li salts for the increment of selectivity towards the meso stereoisomer of DTHFP, either using the published conditions or choosing conditions more appropriate to our chemical process.

In the present disclosure all figures rounded to the nearest whole % unless decimals otherwise provided. All temperatures and temperatures of properties are at 20° C. unless otherwise specified. All pressures are 101 kPa (1 atm pressure) unless otherwise specified.

In the present document quantities when presented in equivalent units are represented by the quantity presented in the first set of units and subsequent units, such as those in brackets using the measurement systems are presented for information only.

The nomenclature X %-Y % provides the maximum and minimum values obtained in repeat experiments. Any quantity for which the units are not specified is a quantity by weight in grams.

What is claimed is:

1. A method of diastereoselective hydrogenation, the method comprising providing a substrate of formula:

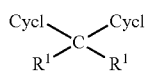  (1)

wherein Cycl represents a cyclic moiety selected from the group consisting of furan ($C_4H_3O$—) and 4H-pyran ($C_5H_6O$—) rings; and R1 is H or C1 to C6 alkyl chain; reacting the substrate with hydrogen under pressure in the presence of a catalyst structure comprising a lithium salt and a metal hydrogenation catalyst on a support, wherein the lithium salt acts as a catalyst that does not undergo any transformation, and wherein the metal hydrogenation catalyst is one or more of platinum, palladium, ruthenium, rhodium and nickel, thereby producing a hydrogenation product having a higher meso isomer content than 50%.

2. The method of claim 1, wherein more than 52% meso isomer is produced.

3. The method of claim 1, wherein more than 56% meso isomer is produced.

4. The method of claim 1, wherein the substrate is 2,2-di(2-furyl)propane and the hydroenation product is 2,2'-di(2-tetrahydrofuryl)propane.

5. The catalyst composition of claim 1, wherein the catalyst is palladium.

6. The method of claim 1, wherein the support is selected from the group consisting of carbon, alumina, silica, titanium dioxide, calcium carbonate, lithium aluminate and barium sulfate.

7. The method of claim 6, wherein the support is selected from the group consisting of carbon and alumina.

8. The method of claim 1, wherein the lithium salt is selected from the group consisting of an organo-carboxylate, an organo-sulfate, aluminate, hydroxide, chloride, bromide, carbonate, borate and a mixture thereof.

9. The method of claim 8, wherein the lithium salt is selected from the group consisting of lithium tetraborate, lithium metaborate, and hydrates thereof.

10. The method of claim 1 wherein the method is performed in the presence of a solvent selected from the group consisting of heptane, MTBE, THF, ethyl acetate, methanol, ethanol and isopropanol.

11. The method of claim 10, wherein the solvent is isopropanol.

12. The method of diastereoselective hydrogenation of claim 1 wherein:
the substrate is 2, 2-di(2-furyl)propane, the catalyst is palladium;
the support is selected from the group consisting of carbon, alumina, silica, titanium dioxide, calcium carbonate, lithium aluminate and barium sulfate; and
the lithium salt is selected from the group consisting of an organo-carboxylate, an organo-sulfate, aluminate, hydroxide, chloride, bromide, carbonate, borate and a mixture thereof.

13. A catalyst composition for diastereoselective hydrogenation, comprising a metal hydrogenation catalyst on a support in the presence of a lithium salt, wherein:
the metal hydrogenation catalyst is selected from the group consisting of platinum, palladium, ruthenium, rhodium and nickel;
the support is selected from the group consisting of carbon, alumina, silica, titanium dioxide, calcium carbonate, lithium aluminate and barium sulfate; and
the lithium salt is selected from the group consisting of lithium tetraborate, lithium metaborate, and hydrates thereof; and
wherein 60% or more of the meso isomer of

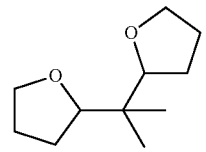

is generated when

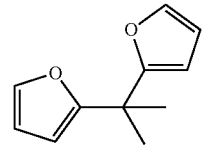

is used as a substrate.

14. The catalyst composition of claim 13, wherein the metal hydrogenation catalyst is palladium.

15. The catalyst composition of claim 13, wherein the support is alumina.

16. The catalyst composition of claim 13, wherein the lithium salt is selected from the group consisting of anhydrous lithium metaborate and lithium metaborate monohydrate.

* * * * *

UNITED STATES PATENT AND TRADEMARK OFFICE
CERTIFICATE OF CORRECTION

Page 1 of 2

PATENT NO. : 10,000,460 B2
APPLICATION NO. : 15/470691
DATED : June 19, 2018
INVENTOR(S) : David Dunn It is certified that error appears in the above-identified patent and that said Letters Patent is hereby corrected as shown below:

On the Title Page

Column 1, Item (*) Notice, Line 3, change "0 days. days." to --0 days.--

Column 1, Item (63), Related U.S. Application Data, Line 4, below "9,751,848." insert as a new item --Sep. 26, 2014 (GB) 1417035.1--

In the Specification

In Column 1, Line 35, change "band" to --bond--

In Column 1, Line 36, change "band" to --bond--

In Column 2, Line 4, change "aver" to --over--

In Column 2, Line 35, change "band" to --bond--

In Column 4, Line 11, change "far" to --for--

In Column 4, Line 63, change "cylohexanone" to --cyclohexanone--

In Column 5, Line 46, change "far" to --for--

In Column 6, Line 4, change "band" to --bond--

In Column 6, Line 23, change "far" to --for--

In Column 6, Line 30, change "100 pmm" to --100 ppm--

Signed and Sealed this
Thirteenth Day of November, 2018

Andrei Iancu
*Director of the United States Patent and Trademark Office*

CERTIFICATE OF CORRECTION (continued)
U.S. Pat. No. 10,000,460 B2

In Column 7, Line 3, change "aver" to --over--

In Column 7, Line 31, change "barate" to --borate--

In Column 8, Line 50, change "palar" to --polar--

In Column 8, Line 53, change "palar" to --polar--

In Column 9, Line 32, change "aver" to --over--

In Column 9, Line 65, change "far" to --for--

In Column 10, Line 14, change "mesa" to --meso--

In Column 10, Line 43, change "isopropylidine" to --isopropylidene--

In Column 11, Line 5, change "(terahydrofuran)," to --(tetrahydrofuran),--

In Column 11, Line 6, change "palar" to --polar--

In Column 12, Line 5 (Approx.), change "invention" to --invention.--

In Column 12, Line 63, change "H1" to --$H^1$--

In Column 13, Line 7, change "far" to --for--

In Column 13, Line 10, change "FIO" to --FID--

In Column 13, Line 12 (Approx.), change "far" to --for--

In Column 13, Line 13 (Approx.), change "far" to --for--

In Column 13, Line 41, change "with with" to --with--

In Column 14, Line 26 (Approx.), change "Metaborete" to --Metaborate--

In Column 14, Line 30 (Approx.), change "Chtoride" to --Chloride--

In Column 14, Line 63, change "far" to --for--

In Column 18, Line 6 (Approx.), change "Stiming" to --Stirring--

In the Claims

In Column 19, Line 32, Claim 4, change "hydroenation" to --hydrogenation--